(12) United States Patent
Bagchi et al.

(10) Patent No.: US 8,173,593 B2
(45) Date of Patent: May 8, 2012

(54) METHODS AND COMPOSITIONS FOR EMERGENCY CONTRACEPTION USING ENDOTHELIN RECEPTOR ANTAGONISTS

(75) Inventors: Indrani C. Bagchi, Champaign, IL (US); Regine Sitruk-Ware, New York, NY (US)

(73) Assignee: The Population Council, Inc., New York, NY (US)

( * ) Notice: Subject to any disclaimer, the term of this patent is extended or adjusted under 35 U.S.C. 154(b) by 420 days.

(21) Appl. No.: 11/988,930

(22) PCT Filed: Jul. 19, 2006

(86) PCT No.: PCT/US2006/028031
§ 371 (c)(1),
(2), (4) Date: Mar. 19, 2009

(87) PCT Pub. No.: WO2007/012006
PCT Pub. Date: Jan. 25, 2007

(65) Prior Publication Data
US 2009/0203591 A1    Aug. 13, 2009

Related U.S. Application Data

(60) Provisional application No. 60/700,455, filed on Jul. 19, 2005.

(51) Int. Cl.
*A61K 38/00* (2006.01)
*A61P 15/08* (2006.01)
*A61P 15/16* (2006.01)
*A61P 15/18* (2006.01)
(52) U.S. Cl. ........................................................ 514/9.8
(58) Field of Classification Search .................. None
See application file for complete search history.

(56) References Cited

U.S. PATENT DOCUMENTS

| 4,670,426 A | 6/1987 | Zor et al. |
| 5,811,416 A | 9/1998 | Chwalisz et al. |

FOREIGN PATENT DOCUMENTS

| WO | 2004037235 | 5/2004 |

OTHER PUBLICATIONS

Pepke-Zaba et al., The Endothelin System and Its Role in Pulmonary Arterial Hypertension (PAH), Throax 2005, vol. 60, pp. 443-444.
Gemzell-Danielsson K et al, Human Reproduction Update, 10(4); 341-348 (2004).
Madsen K M et al:, Journal of the Society for Gynecologic Investigation, 8(4); 239-244 (2001).
European Search Report, EP 06 78 7856.
International Search Report, PCT/US06/28031.

*Primary Examiner* — Marcela M Cordero Garcia
(74) *Attorney, Agent, or Firm* — Lerner, David, Littenberg, Krumholz & Mentlik, LLP

(57) ABSTRACT

Disclosed are methods and compositions containing endothelin receptor antagonists for emergency contraception.

15 Claims, No Drawings

METHODS AND COMPOSITIONS FOR EMERGENCY CONTRACEPTION USING ENDOTHELIN RECEPTOR ANTAGONISTS

CROSS REFERENCE TO RELATED APPLICATIONS

The present application is a national phase entry under 35 U.S.C. §371 of International Application No. PCT/US2006/028031, filed Jul. 19, 2006, published in English, which claims benefit of U.S. Provisional Patent Application No. 60/700,455, filed Jul. 19, 2005. The disclosures of all of said applications are incorporated by reference herein.

BACKGROUND OF THE INVENTION

Several devices and pharmaceutical compositions are available for the prevention of undesirable conception in the case of regular sexual activity. Condoms, pessaries, intrauterine devices as well as different mono or multi-phasic oral contraceptives are some examples of contraceptives that are effective in preventing unwanted conception.

However, in the case of unprotected sexual intercourse, coitus with imperfect contraception (for example, a damaged or torn condom) or possibly victims of rape, action must be taken to prevent conception, soon after exposure. Emergency contraception is a method of preventing pregnancy post-coitus.

Ovulation results from a cascade of events including but not limited to releases of hormones, activation of transcription mechanisms as well as physiological changes. A surge of luteinizing hormone (LH) commences the process of ovulation. The pinnacle of ovulation is the follicle rupture and release of an oocyte from the ovary. After release of the oocyte, well-defined and vascularized structures form in the ovary from the encasement (differentiated thecal and granulosa cells) of the oocyte termed the corpora lutea. This structure releases the hormone progesterone.

The use of levonorgestrel in emergency contraception was discovered a few decades ago. The results of the studies were reported in two well-documented publications [*Lancet* 1998; 352: 428-33, and Ho, et al., Human Reproduction 8(3): 389-92 (1993)]. The efficacy of tablets containing only 0.75 mg of levonorgestrel and the combined tablets of the Yuzpe method containing 0.1 mg of ethinyl-estradiol+1.0 mg levonorgestrel were studied by administering the doses 12 hours apart within 48 as well as within 72 hours of unprotected coitus. The results showed that protection with two tablets containing 0.75 mg of levonorgestrel was better than with the Yuzpe regimen, but the women, who received only levonorgestrel, observed less side effects, which could be due to the lack of ethinyl-estradiol.

The mechanism of action of levonorgestrel used as post-coital contraceptive was investigated in several studies. Keserü, et al., Contraception 10(4):411-24 (1974), report that the anti-ovulatory effect probably depends partly on the time elapsed between talking the last tablet and the time of ovulation, partly on the quantity of the applied hormone. According to other authors, factors other than the inhibition of ovulation can also influence the contraceptive effect [Hapangama, et al., Contraception 63:123-29 (2001)]. Levonorgestrel administered in the follicular phase decreased the proliferation activity of the endometrium, while in the luteal phase there was no effect [Landgren, et al., Contraception 39(3):275-89 (1989)].

Several trials were conducted to show the effect of levonorgestrel on the cervical mucus, which could be observed a few hours after the administration. Levonorgestrel inhibits the sperms getting into the upper genital tract in such a way that it causes the thickening of the cervical mucus almost immediately after the absorption of the hormone. It was also shown that after the administration of 400 μg of levonorgestrel the alkalization of the intrauterine fluid starts already after 4 hours of administration and it lasts for approximately 48 hours. This effect can play a role in the inhibition of the movement of sperms and their entry into the uterine cavity, and as a consequence, in the contraceptive effect as well [Spona, et al., Contraception 11(1):31-43 (1975)].

The studies showed that two pharmaceutical compositions containing 0.75-0.75 mg of levonorgestrel used at 12 hours' interval within 72 hours after the unprotected coitus successfully inhibited the conceptions which otherwise might have occurred. The efficacy was significantly better than the efficacy of the Yuzpe regimen used worldwide earlier. Because of the lack of the estrogen component, side effects (nausea, feeling of sickness, vomiting) leading to the decrease in compliance and the efficacy of the treatment were observed far, less frequently. The results of the clinical studies showed that the efficacy was the better the earlier the treatment started after the coitus. However, according to experience, if women wanted to follow the instructions correctly, they often delayed taking the first tablet so as taking the second dose after 12 hours would not fall on an extremely inconvenient time (for example 3 o'clock in the morning). The results of the studies showed that the prescription of the 12 hour interval between the two doses decreased the compliance. According. to statistical data, the majority of women took the second dose within 12 to 16 hours after the first one [*Lancet* 1998; 352: 428-33]. More recently, a study from the WHO showed that intake of the 2 doses at the same time did not differ in efficacy as compared with the 2 doses taken 12 h apart, and therefore this newly proposed single dose regimen would have a better acceptability for EC use [von Hertzen, et al., Lancet 360: 1803-10 (2002)].

In Ortiz, et al., Hum. Reprod. 19(6):1352-56 (2004), it was concluded that levonorgestrel exerts its EC effect by inhibiting or delaying ovulation.

Mifepristone (RU-486) has been used as an emergency contraceptive by inhibiting ovulation. Sarkar, Acta Obstet Gynecol Scand 84(4):309-16 (2005), describes the potential of RU-486 as an emergency contraceptive drug. Post-coital contraceptive pills are also disclosed in U.S. Pat. No. 4,670,426, and which contain a progesterone antagonist such as RU-486 and a blocker of estrogen synthesis. Gemzell-Danielsson et al., Hum. Reprod. Update 10(4):341-8 (2004), describes the mechanisms of action of mifepristone and levonorgestrel when used for emergency contraception.

SUMMARY OF THE INVENTION

A first aspect of the present invention is directed to a method for emergency contraception, comprising administering to a female in need thereof an effective amount of an endothelin receptor antagonist.

A related aspect of the invention is directed to a method for inhibiting ovulation in a female post-coitus, comprising administering to a female in need thereof an effective amount of an endothelin receptor antagonist.

Another aspect of the present invention is directed to an intravaginal drug delivery system, comprising an amount of an endothelin receptor antagonist effective to achieve emergency contraception.

DETAILED DESCRIPTION OF THE INVENTION

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin-converting enzyme (ECE). Endothelin-1 (ET-1) was first isolated from the culture of supernatant of porcine aortic endothelial cells. Subsequent studies, including human genomic analysis, identified two additional structurally and functionally related isopeptides named ET-2 and ET-3 (Ishikawa et al., Proc. Natl. Acad. Sci. USA 91:4892-96 (1994) (hereinafter "Ishikawa"). Two distinct G protein-coupled receptor subtypes known as endothelin receptor A (ETRA), a 427 amino acid polypeptide (disclosed in references 6-8 of Ishikawa) and endothelin receptor B (ETRB), a 442 amino acid polypeptide disclosed in references 9-13 of Ishikawa) mediate the diverse effects of endothelin. See also, Arai, et al., Nature 348, 730 (1990). By "G protein-coupled receptor" herein is meant a signal receptor protein in the plasma membrane that responds to the binding of a signal molecule by activating a G protein. The ETRA subtypes bind ET-1 and ET-2 with higher affinity than ET-3 whereas, the ETRB subtypes have similar affinities for all isoforms of ET.

The emergency contraceptive agents of the present invention are endothelin receptor antagonists. As used herein, the term "antagonist" herein is meant an agent that inhibits endothelin receptor activity. Preferably, the ETR is an ETRB antagonist in that it selectively inhibits ETRB. Preferred ETRB antagonists include BQ788 (N-cis-2,6-dimethylpiperidinocarbonyl-L-gamma-methylleucyl-D-1-methoxycarbonyltryptophanyl-D-norleucine), and its derivatives. The biochemical and pharmacological profile and structure of BQ788, as well as methods of preparation are described in Ishikawa, Karaki, et al., Biochem. Biophys. Res. Comm. 205, 168 (1994), and U.S. Pat. No. 6,545,048 (which also discloses derivatives of BQ788, which are functionally equivalent to BQ788 and have ETR, preferably ETRB inhibitor activity). BQ-788 is also commercially available from the Sigma Company (product number B-157 in Sigma's Biochemicals and Reagents 2000-2001). Applicants have also found that BQ788 inhibits function of endothelin-2.

Other ETB antagonists include A192621.1 ((2R,3R,4S)-2-(4-Propoxyphenyl)-4-(1,3-benzodioxol-5-yl)-1-(2,6-diethylphenylaminocarbonylmethyl)-pyrrolidine-3-carboxylic acid) (Brodsky, et al., J. Cardiovasc. Pharmacol. 36(5 Suppl. 1):S11-3 (2000)), RES701-1 (a cyclic peptide produced by *Streptomyces* sp. RE-701 (cyclic (Gly1-Asp9) (Gly-Asn-Trp-His-Gly-Thr-Ala-Pro-Asp-Trp-Phe-Phe-Asn-Tyr-Tyr-Trp), as described in Morishita, et al., J. Antibiot (Tokyo) 47(3): 269-275 (1994)), Ro46-8443 (N-[6-[(2R)-2,3-Dihydroxypropoxy]-5-(2-methoxyphenoxy)-2-(4-methoxyphenyl)-4-pyrimidinyl]-4-(1,1-dimethylethyl)-benzenesulfonamide) (a non-peptide antagonist described in Breu, et al., FEBS Lett. 383(1/2):37-41 (1996)), IRL1083, PD142983, RES7013, and IRL2500. See also, Goto, et al., "New Expansion of endothelin research: perspectives for clinical application of endothelin-receptor antagonists," in Folia Pharmacologica Japonica 121(2):91-101 (2003). Thus, the antagonists include peptides and non-peptide agents.

In some embodiments, the ETR antagonist is an ETRA antagonist and selectively inhibits ETRA. ERTA antagonists include but not limited to LU135252 ((+)-(S)-2-(4,6-Dimethoxy-pyrimidin-2-yloxy)-3-methoxy-3,3-diphenyl-propionic acid)), BQ485 (N—(N—(N-((Hexahydro-1H-aepin-1-yl)carbonyl)-L-leucyl-D-tryptophyl)-D-tryptophan), BQ123 (Cyclo(D-α-aspartyl-L-prolyl-D-valyl-L-leucyl-D-tryptophyl)), FR139317 ((R)2-[(R)-2-[(S)-2-[[1-(Hexahydro-1H-azepinyl)]carbonyl]amino-4-propionyl] amino-3-(2-pyridyl)propionic acid), BE18257B (Cyclo(L-alanyl-D-alloisoleucyl-L-leucyl-D-tryptophyl-D-alpha-glutamyl)), JKC301, JKC302, BQ610 (N-[1-Formyl-N—[N-[(hexahydro-1H-azepin-1-yl)carbonyl]-L-leucyl]-D-tryptophyl]-D-tryptophan), PD156707 (Sodium 2-benzo[1,3] dioxol-5-yl-4-(4-methoxyphenyl)-4-oxo-3-(3,4,5-trimethoxybenzyl)-but-2-enoate), A127722 (trans,trans-2-(4-Methoxyphenyl)-4-(1,3-benzodioxol-5-yl)-1-(N,N di(n-butyl)aminocarbonylmethyl)-pyrrolidine-3-carboxylic acid), Ro61-1790, TBC11251 (N-(4-Chloro-3-methyl-5-isoazolyl)-2-[(6-methyl-1,3-benzodioxol-5-yl)acetyl]-3-thiophenesulfonamide), SO139, SB234551, A192621 ((2R, 3R,4S)-2-(4-Propoxyphenyl)-4-(1,3-benzodioxol-5-yl)-1-(2,6-diethylphenylaminocarbonylmethyl)-pyrrolidine-3-carboxylic acid), ABT627 ((2R,3R,4S)-(+)-2-(4-Methoxyphenyl)-4-(1,3-benzodioxol-5-yl)-1-(N,N-di(n-butyl)aminocarbonylmethyl)-pyrrolidine-3-carboxylic acid), A216546 ([2S-(2,2-Dimethylpentyl)-4S-(7-methoxy-1,3-benzodioxol-5-yl)-1-(N,N-di(n-butyl)aminocarbonylmethyl)-pyrrolidine-3R-carboxylic acid), PD155080, BMS182874 (5-(dimethylamino)-N-(3,4-dimethyl-5-isoxazolyl)-1-haphthalenesulfonamide), 97139, LU127043, IRL1620 (N-Suc-[Glu9,Ala11,15]-Endothelin-1(8-21)), and PD151242 (N—[N—[N-[(Hexahydro-1H-azepin-1-yl)carbonyl]-L-leucyl]-1-methyl-D-tryptophyl]-D-tyrosine).

In yet other embodiments, the ETR antagonist is a non-selective antagonist in that it binds to more than one ETR. Examples of these ETR antagonists are: A186086 ((2R,3R, 4S)-2-(3-Fluoro-4-methoxyphenyl)-4-(1,3-benzodioxol-5-yl)1-(2-(N-propyl-N-pentanesulfonylamino)ethyl)-pyrrolidine-3-carboxylic acid), Ro61-0612 (5-Isopropyl-pyridine-2-sulfonic acid 6-(2-hydroxy-ethoxy)-5-(2-methoxyphenoxy)-2-(2-1H-tetrazol-5-yl-pyridin-4-yl)-pyrimidin-4-ylamide), SB209670 ((±)-(1S,2R,3S)-3-(2-Carboxymethoxy-4-methoxyphenyl)-1-(3,4-methylenedioxyphenyl)-5-(prop-1-yloxy)-indane-2-carboxylic acid), SB217242 (1-(1,3-Benzodioxol-5-yl)-2,3-dihydro-3-[2-(2-hydroxyethoxy)-4-methoxyphenyl]-5-propoxy-,-1H-indene-2-carboxylic acid), PD142983 (N-Acetyl-β-Phenyl-D-Phe-Leu-Asp-Ile-Ile-Trp), PD145065 (N-Acetyl-α-[10,11-Dihydro-5H-dibenzo[a,d] cycloheptadien-5-yl]-D-Gly-Leu-Asp-Ile-Ile-Trp), Ro47-0203 (4-Tert-butyl-N-[6-(2-hydroxy-ethoxy)-5-(2-methoxyphenoxy)-2,2'-bipyrimidin-4.-yl]-benzenesulfonamide), BE18257A/W7338A (Cyclo(L-alanyl-D-valyl-L-leucyl-D-tryptopyl-D-alpha-glutamyl)), Ro462005 ((4-(1,1-dimethyl-ethyl)-N-(6-(2-hydroxyethoxyl)-5-(3-methoxyphenoxy)-4-pyrimidinyl)benzenesulfonamide), PD156252, LU302872, TAK044 (Cyclo(L-alpha-aspartyl-(2R)-2-(2-thienyl)glycyl-L-leucyl-D-tryptophyl-D-alpha-aspartyl-(alpha-S)-alpha-amino-gamma-oxo-4-phenyl-1-piperazinebutanoyl), disodium salt), A182086, L744453, and L754142.

The chemical structure and additional properties of various ETR antagonists are described in U.S. Pat. Nos. 5,284,828; 5,378,715; and 5,382,569. The role of ET and ETRs in various physiological and pathophysiological conditions has been studied extensively and described in U.S. Pat. Nos. 6,462,194 and 5,550,110.

The drug is most conveniently administered orally e.g., in the form of tablets, capsules, pills, solutions or suspensions. Oral administration offers greater convenience and acceptability. Formulations or compositions intended for oral use may be prepared according to methods known to the art. Such compositions may contain one or more agents selected from the group consisting of sweetening agents, flavoring agents, coloring agents and preserving agents in order to provide pharmaceutically elegant and palatable preparations, and include a pharmaceutically acceptable carrier. The oral administrations may be in the form of a pill/tablet, capsule (e.g., gelcaps), elixir, syrup, suspension lozenge or troche. Syrups and elixirs may be formulated with sweetening agents, for example glycerol, propylene glycol, sorbitol or sucrose. Such formulations may also contain a demulcent, a preservative, and flavoring and coloring agents.

In tablet or pill form, the formulations contain the one active ingredient in admixture with non-toxic, pharmaceutically acceptable excipients that are suitable for the manufacture of tablets. For example, these excipients may be inert diluents, such as calcium carbonate, sodium carbonate, lactose, calcium phosphate or sodium phosphate, granulating and disintegrating agents (e.g., corn starch or alginic acid), binding agents (e.g., starch, gelatin or acacia), and lubricating agents (e.g., magnesium stearate, stearic acid or talc). These oral dosage forms may be uncoated or they may be coated by known techniques to delay disintegration and absorption in the gastrointestinal tract and thereby, provide a sustained action over a longer period. For example, a time delay material such as glyceryl monosterate or glyceryl distearate may be employed.

Formulations for oral use may also be presented as hard gelatin capsules, in which the active ingredient is mixed with an inert solid diluent (e.g., calcium carbonate, calcium phosphate or kaolin) or as soft gelatin capsules, in which the active ingredient is mixed with water or an oil medium (e.g., peanut oil, liquid paraffin or olive oil).

Aqueous suspensions contain the active materials in admixture with excipients suitable for the manufacture of aqueous suspensions. Such excipients may be suspending agents (e.g., sodium carboxymethylcellulose, methylcellulose, hydropropylmethylcellulose, sodium alginate, polyvinylpyrrolidone, gum tragacanth and gum acacia) or dispersing or wetting agents, such as a naturally-occurring phosphatide (e.g., lecithin), condensation products of an alkylene oxide with fatty acids (e.g., polyoxyethylene stearate), condensation products of ethylene oxide with long chain aliphatic alcohols (e.g., heptadecaethyleneoxycetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also. contain one or more preservatives (e.g., ethyl or n-propyl p-hydroxybenzoate), one or more coloring agents, one or more flavoring agents, and one or more sweetening agents, such as sucrose or saccharin.

oily suspensions may be formulated by suspending the active ingredients in a vegetable oil, such as arachidic oil, olive oil, sesame oil or coconut oil, or in a mineral oil, such as liquid paraffin. The oily suspensions may contain a thickening agent, such as beeswax, hard paraffin or cetyl alcohol. Sweetening agents, such as those set forth above, and flavoring agents may be added to provide palatable oral preparations. These compositions may be preserved by the addition of an antioxidant such as ascorbic acid.

Suitable dispersible powders and granules for the aqueous suspension are prepared by the addition of water, and provide the active ingredient in admixture with a dispersing or wetting agent, suspending agent and one or more preservatives. Suitable dispersing or wetting agents and suspending agents are exemplified by those already mentioned above. Additional excipients such as sweetening, flavoring and coloring agents may also be present.

Oral formulations of the invention may also be in the form of oil-in-water emulsions. The oily phase may be a vegetable oil (e.g., olive oil or arachidic oil), a mineral oil (e.g., liquid paraffin) or mixtures thereof. Suitable emulsifying agents may be naturally occurring gums (e.g., gum acacia or gum tragacanth), naturally occurring phosphatides (e.g., soy bean, lecithin, and esters or partial esters derived from fatty acids and hexitol), anhydrides (e.g., sorbitan monoleate), and condensation products of partial esters with ethylene oxide (e.g., polyoxyethylene sorbitan monoleate). The emulsions may also contain sweetening and flavoring agents.

The drug can also be administered non-orally such as intravaginally (e.g., via vaginal rings, gels, jellies, creams, suppositories or foams) or in the uterus via intrauterine medicated systems. Vaginal rings that produce an initial burst of the EC agent, followed by release of a relatively consistent amount of drug per day may offer the dual advantage of acting as an EC and as a long-term contraceptive. Vaginal rings are annularly shaped articles made of inert elastomeric materials that can be introduced into the vagina in a simple manner without medical assistance. The ring fits between the rear wall of the vagina and the upper edge of the pubic bone. Numerous types of vaginal rings have been described in the patent and non-patent literature alike. See, e.g., U.S. Pat. Nos. 4,012,496 and 4,155,991 (both to Schopflin et al.); U.S. Pat. No. 4,292,965 (Nash) (which teaches three-layered rings); U.S. Pat. No. 3,545,439 (Duncan); U.S. Pat. No. 3,920,805 (Roseman); U.S. Pat. Nos. 3,991,760 and 3,995,634 (both to Drobish et al.); U.S. Pat. No. 3,995,633 (Gougen); U.S. Pat. Nos. 4,250,611 and 4,286,587 (both to Wong); U.S. Pat. No. 4,596,576 (de Nijs); WO95/00199 (Lehtinen et al.); NL 8500-470-A; and Apter, et al., Contraception 42:285-295 (1990); Burton, et al., Contraception 17:221-230 (1978); Burton et al., contraception 19:507-516 (1979); Jackanicz, Contraception 24:323-339 (1981); Sivin, et al., Contraception 24:341-358 (1981); Timmer, et al., Contraception 43:629-642 (1990); Toivonen, Contraception 20:511-518 (1979); and Sitruk-Ware, et al., Contemporary Clin. Gynecol. & Obstet. 2:287-98 (2002).

Many basic ring designs are known in the art, e.g., the homogeneous ring, two-layered rings, the Roseman ring and: three-layered rings. See, e.g., Weiner et al., Acta Obstet Gynecol. Scand, Suppl. 54, 1977 p. 35; U.S. Pat. No. 3,920, 805 to Roseman and U.S. Pat. No. 4,012,496 to Schopflen. The polymeric materials, e.g., polymers and resins, are physiologically acceptable and inert, as those terms are generally understood by persons in the art. In the homogeneous ring, the contraceptive agent is substantially uniformly dispersed throughout an inert elastomer matrix. See, e.g., U.S. Pat. No. 3,545,439 to Duncan and Victor, et al., Contraception 12:261, 1975. Two-layered rings contain a polymeric material e.g., an elastomer ring encircled by a second ring of inert physiologically acceptable synthetic resin or elastomer containing (e.g., impregnated with or having dispersed therein so as to form a matrix) a contraceptive agent. See, e.g., U.S. Pat. No. 4,012, 496 to Schoepflin, et al. In the Roseman ring, a thin layer of an inert elastomer containing a contraceptive agent is molded onto a central inert core of elastomer. Three-layered rings contain a layer of an inert elastomer containing a contraceptive agent that surrounds a central inert core of synthetic elastomer, which in turn is surrounded by an outer layer of inert elastomer of variable thickness to control the release rate of the contraceptive agent. Yet another vaginal ring design is taught in U.S. Pat. No. 5,972,372. This patent teaches a vaginal ring which contains a vaginal ring body of a first polymeric material having at least one hollow internal channel defining an opening to the exterior of said body and which channel is adapted to receive a core containing an intravaginally administrable drug through the opening, and a core positioned in the channel, wherein the core contains a pharmaceutically effective amount of at least one intravaginally administrable drug dispersed in the second polymeric material. The first and second polymeric materials may be the same or different. The '372 patent also contains illustrations of shell rings, homogeneous rings, and core rings (a ring having at least two non-extensive cores, each of which may contain the same or different active agents).

A variety of physiologically acceptable resins or elastomers have been disclosed in the literature as being suitable for making vaginal rings, including silicone elastomers such as polyorganosiloxanes, e.g., polydimethylsiloxane or a copolymer of dimethylsiloxane and methylvinylsiloxane, conventional silicone rubber, polyurethanes, SILASTIC 382 (Dow Corning), latex rubber, polyamides, polyesters, polytetrafluoroethylene, polyethylene vinyl acetate and nylon. The vaginal rings of the present invention preferably contain silicone elastomers, and more preferably silicone rubbers such as medical grade organopolysiloxanes, such as among the following:

1. Thermosetting organopolysiloxanes to be vulcanized with peroxide curing catalysts, e.g. benzoyl peroxide or di-p-chlorobenzoyl peroxide at temperatures of about 200.degree. C. and requiring a heat after-treatment, e.g. those described in U.S. Pat. Nos. 2,541,137; 2,723,966; 2,863,846; 2,890,188 and 3,022,951.
2. Hydroxyl-terminated organopolysiloxanes of the RTV (room temperature vulcanizing) type which harden to elastomers at room temperature after the addition of cross-linking agents in the presence of curing catalysts and under the atmospheric humidity. Typical curing catalysts are metallic salts of carboxylic acids, preferably tin salts, e.g. tin (II) octoate and tin (II)-2-ethylhexanoate.
3. Single-component silicone rubber compositions which are cured at room temperature under atmospheric humidity without any further additives. These single component compositions contain primarily organopolysiloxanes with two terminal-positioned hydrolyzable acyloxy groups, e.g. acetoxy; the acyloxy groups are hydrolyzed under atmospheric humidity to form trifunctional siloxane units which crosslink the polymer into a cured elastomer. Such organopolysiloxanes are described, e.g., in U.S. Pat. Nos. 2,927,907 and 3,035,016 and in British Patents 798,669 and 804,199.
4. Two-component dimethylpolysiloxane compositions, platinum-catalyzed at room temperature or under slightly elevated temperature and capable of addition cross-linking. The medicated layer can be constructed from an elastomer selected from classes 2 and 3 above and the outer layer can be constructed from an elastomer selected from classes 1 to 4 above, provided the elastomers in class 1 are cured before coming in contact with the medicated layer. The preferred elastomers for use in the core, medicated layer and the outer layer are polydimethylsiloxanes.

The dimensions of the vaginal rings can be determined by persons skilled in the art using standard techniques. In general, the vaginal ring typically has an overall diameter of about 40 mm to about 70 mm, preferably from 50 mm to 65 mm, and more preferably about 58 mm. The overall cross sectional diameter of the ring generally ranges from about 2 mm to about 10 mm, and preferably about 6 to 8 mm, and more preferably about 4 to about 8 mm. Thus, the thickness of the inert core generally ranges from about 1 mm to about 9 mm; the thickness of the drug-containing layer generally ranges from about 0.5 mm to about 2.0 mm; and in the case of three-layered rings, the thickness of the outer layer generally ranges from about 0.05 mm to about 0.6 mm, preferably about 0.1 mm to about 0.3 mm. The thickness of the outer layer affects the distance the drug must travel to reach the vaginal tissues. Thus, it can be varied to control the release rate of the drug.

The vaginal rings of the present invention may be prepared in accordance with standard techniques. For example, methods of preparing vaginal rings are described in U.S. Pat. No. 4,292,965. In some embodiments, the ring is prepared first by mixing or dispersing the drug in the elastomer, e.g., to form a matrix. Once the drug is mixed with the matrix material to achieve a substantially uniform dispersion, the desired shape of the resultant dispersion is achieved by molding, casting, extrusion, or other appropriate process. In the case of a three-layered ring, for example, the dispersion may be filled into a rubber tube (e.g., silicone) containing an elastomeric core, followed by joining the two ends of the tube to form a ring. Another method involves co-extrusion. In these embodiments, the layers of elastomer, one of which contains the drug, are co-extruded and then cured by heating at a temperature below the melting point of the drug. Suitable medical adhesives include medical grade Silicone Type A.

The compositions of the present invention may also take the form of a non-vaginal ring sustained release composition, e.g., creams, gels, jellies, foams and suppositories (e.g., effervescent suppositories) that will provide the required release of the endothelin receptor antagonist, e.g., BQ788. Each of these compositions will contain at least one pharmaceutically acceptable excipient, carrier or diluent. Persons skilled in the art may select appropriate ones to make the various types of sustained-release compositions e.g., by resort to standard texts in the art. For example, a vaginal cream according to the invention may contain a hydrocarbon base (e.g. white petrolatum), a solvent (e.g. glycerin or propylene glycol) and an emulsifier (e.g. cetyl alcohol, stearyl alcohol, sodium lauryl sulphate). A vaginal jelly may contain a solvent (e.g. glycerin or propylene glycol) a gel forming agent (e.g. sodium alginate (especially with calcium ions), tragacanth, gelatin, methyl cellulose, sodium carboxymethylcellulose, carbomer and polyvinyl alcohol) and a non-spermicidal or non sperm-immobilising preservative. Vaginal foam may contain a fluorinated hydrocarbon propellant and a surfactant or emulsifier. Numerous examples of these types of compositions are known in the art. See, e.g., WO 03/093,322, and U.S. Pat. Nos. 5,595,980; 4,585,647; 4,368,186; 5,766,681; 6,207,696; 4,310,510; and 4,795,761. These compositions may further contain one or more other active agents, e.g., a spermicide.

Performance of a gel depends on such factors as solubility of the active agent, selection of enhancer and gelling components and stability of the resultant formulation. Alcohols should be avoided. Gelling agents include hydroxylpropylmethylcellulose, carbopol, and carboxymethyl cellulose. The compositions may further include a pH-adjusting agent in an amount to make the formulation compatible with the vaginal environment. In general, formulations having a pH of about 5 to about 6 are suitable for vaginal administration.

Other routes of administration such as transdermal, topical or enteral, may be used if desired or practical under the circumstances.

In some embodiments, the antagonists may be administered in the form of conjugates or fusion proteins in order to specifically target follicular cells. The antagonist may therefore be coupled e.g., chemically conjugated, to a ligand such as follicle stimulating hormone (FSH) that selectively targets follicular cells. Depending on the nature of the endothelin receptor antagonist (peptide or non-peptide, the preparation of the conjugates or fusion proteins may be performed on the genetic level (by fusing gene fragments encoding the ETR antagonist and the ligand and then harvesting the expression product from a suitable host) or at the protein level (by chemically conjugating the respective entities), each in accordance with standard techniques.

The drug can be administered as a single dose or divided (e.g., 2 or 3) doses taken at suitable time intervals (e.g., 12 hours). To achieve emergency contraception, the drug can be administered up to about 5 days after coitus. It is preferably administered as soon as practical thereafter and most preferably within about 3 days after coitus. One of the advantages of the present invention is that inhibition of ETR even very late in the process of ovulation is still effective in preventing the ovulatory peak of luteinizing hormone (LH).

Dosages and desired drug concentrations of pharmaceutical compositions of the present invention may vary depending on several factors, including the weight of the patient and her overall health, the potency of the ETR antagonist, and the route of administration (e.g., and whether hepatitic metabolism is involved). The appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., Eds., Pergamon Press, New York 1989, pp. 42-96. The term "contraceptively effective" amount as used herein refers to the amount needed to perform the particular treatment, which is emergency contraception. Amounts of the drug generally range from about 0.1 mg to about 300 mg/day. In some embodiments, the amount generally varies from about 0.5.to about 50 mg/day. In some other embodiments, the amount generally varies from about 10 mg/day to about 200 mg/day, and in others, the amount generally varies from about 10 mg/day to about 50 mg/day. In preferred embodiments, the drug is orally administered as a one-time dose.

The methods and compositions of the present invention may be used by females who have had unprotected sex, in situations where condoms broke, slipped or were used incorrectly, when on or several pills of a regular oral contraceptive were forgotten, when progestogen-only pills were taken more than three hours late, when the female is more than 2 weeks late for a progestogen-only contraceptive injection, when the female is more than 7 days late for a combined estrogen-plus-progestogen monthly injection, when there is dislodgment, breakage, tearing or early removal of a diaphragm or cervical cap, failed coitus interruptus, failure of a spermicide tablet or film to melt before intercourse, miscalculation of periodic abstinence method or failure to abstain on fertile day of cycle, or IUD expulsion.

EXAMPLES

Without intending to be bound by theory, Applicants believe that the ETR antagonists such as BQ788 exert an EC effect by preventing follicle rupture in the ovary, thus inhibiting ovulation.

In-situ hybridization during superovulation depicted ET-2 specifically localized in the granulosa cells of the preovulatory follicles. This verified the presence of ET-2 and ETRs in the granulosa cells of the late phase ovarian follicle.

Pharmacological blockers of the endothelin receptor system were implemented to elucidate the role of ET-2 during superovulation. JKC301 (ETRA antagonist) and BQ788 (ETB antagonist) were injected 6 hours after hCG injection and an oocyte count was tabulated. BQ-788 proved to be the more effective inhibitor of ovulation by posting a 65% decrease in the number of oocytes compared to 45% by JKC301. BQ788 treatment was further investigated and found to have a time effect. BQ788 posted a 39%, 58%, and 66% decrease in number of oocytes at 4, 6 and 8 hours, respectively, after hCG injection.

BQ788 was further tested to examine the manner in which this ETB antagonist reduced the number of oocytes. Histological sections of ovaries collected at 18 hours after hCG injection in superovulated mice that received either vehicle or BQ788 through i/p at 8 hours after hCG, were examined and found to have striking differences in the number of corpus lutea (photo not shown). The vehicle. demonstrated numerous corpus lutea indicating successful ovulation, while BQ788 demonstrated few corpus lutea and numerous unruptured follicles suggesting the inhibition of ovulation through blockade of follicle rupture. The presence of corpus lutea indicates that the ovulation has taken place while the unruptured follicle shows that the ovulation did not occur.

Without intending to be bound by theory, Applicants believe that the invention works as follows. ET-2 binds to the G-protein-coupled receptor ETRB in the granulosa cells of the late phase ovarian follicle. The now activated G-protein complex stimulates production of progesterone. The progesterone receptor-signaling pathway mediates the surge of LH that triggers follicle rupture, the pinnacle of ovulation.

Addition of the ETR antagonist, BQ788, resulted in inhibition of ovulation by blocking follicle rupture in the ovary, even when given at 8 hours, a stage very close to the ovulation. This result illustrates an advantage of the invention over at least one known EC, namely levonorgestrel (LNG), which is believed not to be effective as an EC when administered at this late stage in ovulation.

All patent and non-patent publications cited in this specification are indicative of the level of skill of those skilled in the art to which this invention pertains. All these publications and patent applications are herein incorporated by reference to the same extent as if each individual publication or patent application was Specifically and individually indicated as being incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of emergency contraception comprising the oral administration to a female in need thereof an effective amount of an endothelin receptor antagonist.

2. The method of claim 1, wherein said endothelin receptor antagonist is an endothelin receptor B (ETRB) antagonist.

3. The method of claim 2, wherein said ETRB antagonist comprises N-cis-2,6-dimethylpiperidinocarbonyl-L-gamma-methylleucyl-D-1-methoxycarbonyltryptophanyl-D-norleucine (BQ788).

4. The method of claim 2, wherein said ETRB antagonist comprises A 192621.1 ((2R,3R,4S)-2-(4-Propoxyphenyl)-4-(1,3-benzodioxol-5-yl)-1-(2,6-diethylphenylaminocarbonylmethyl)-pyrrolidine-3-carboxylic acid), RES701-1 (cyclic (Gly1-Asp9) (Gly-Asn-Trp-His-Gly-Thr-Ala-Pro-Asp-Trp-Phe-Phe-Asn-Tyr-Tyr-Trp), Ro46-8443 (N-[6-[(2R)-2,3-Dihydroxypropoxy]-5-(2-methoxyphenoxy)-2-(4-methoxyphenyl)-4-pyrimidinyl]-4-(1,1-dimethylethyl)-benzenesulfonamide), and IRL2500B Q788.

5. The method of claim 1, wherein said endothelin receptor antagonist comprises an endothelin receptor A (ETRA) antagonist.

6. The method of claim 1, wherein said endothelin receptor antagonist is a non-selective endothelin receptor antagonist.

7. The method of claim 1, wherein said endothelin receptor antagonist is administered orally via an oral dosage form.

8. The method of claim 1, wherein said oral dosage form is a pill.

9. The method of claim 1, wherein said endothelin receptor antagonist is administered orally in a one-time dosage.

10. The method of claim 1, wherein said endothelin receptor antagonist is administered non-orally.

11. The method of claim 10, wherein the endothelin receptor antagonist is administered intra-vaginally or via intrauterine device.

12. The method of claim 1, wherein said endothelin receptor antagonist is administered in the form of a chemical conjugate with follicle stimulating hormone.

13. The method of claim 1, wherein said endothelin receptor antagonist is administered in an amount of 10 mg to 50 mg per day.

14. The method of claim 1, wherein said endothelin receptor antagonist is administered within three days post-coitus.

15. A method for inhibiting ovulation in a female post-coitus, comprising administering to a female in need thereof an effective amount of an endothelin receptor antagonist.

* * * * *